United States Patent [19]

Holden

[11] Patent Number: Plant 7,321

[45] Date of Patent: Sep. 11, 1990

[54] VARIETY OF GERANIUM NAMED GRACE

[75] Inventor: Douglas Holden, Solvang, Calif.

[73] Assignee: Bodger Seeds, Ltd., El Monte, Calif.

[21] Appl. No.: 345,626

[22] Filed: Apr. 28, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden Ziesenheim & Webb

[57] ABSTRACT

A new Geranium cultivar is distinguished by its lateral and procumbent mound and cascading growth habit, compactness, the presence of zoning, the pale pink inflorescence, the use of either hanging basket or ground bed, its heat tolerance, and a much better cutting producer.

1 Drawing Sheet

BACKGROUND OF THE NEW PLANT

The present invention comprises a new and distinct cultivar of Pelargonium known by the varietal name Grace (Oglevee No. 1316, Bodger No. 6GM 129-7). The new variety was discovered in a selective breeding program to develop hybrid varieties for vegetative propagation by Mr. Douglas Holden and is a selection of a cross between the seed parent Salmon Floral Cascade and the pollen parent Pinto Red.

Salmon Floral Cascade is a commercially available vegetatively propagated cutting variety from Australia and which includes strains of *Pelargonium frutetorum* and *Pelargonium peltatum.* Pinto is a commercially available salmon single flower zonal (*Pelargonium* × *hortorum*) $F_1$ hybrid seed geranium.

The new cultivar was discovered in August of 1986 at Bodger Seeds, Ltd. in El Monte, Calif., was first asexually reproduced by cuttings by Bodger Seeds, Ltd. at El Monte, Calif. and has been repeatedly asexually reproduced by cuttings at Oglevee Ltd. in Connellsville, Pa. It has been found to retain its distinctive characteristics through successive propagations.

The new cultivar has a different color (pale-pink) and larger flowers than the closest comparative variety, Salmon Floral Cascade.

The new cultivar, when grown in a glass greenhouse in Connellsville, Pa., using full light, 60° F. night temperature, 68° F. day temperature, 71° F. vent temperature, and grown in a soilless media of constant fertilizer of 200–250 parts per million nitrogen and potassium, has a response time from a rooted cutting to a flowering plant in a four inch (10 cm) pot of six weeks.

DESCRIPTION OF THE DRAWING

The accompanying drawing illustrates a new cultivar, the color being as true as possible with color illustration of this type.

DESCRIPTION OF THE NEW PLANT

The following detailed description set forth the characteristics of the new cultivar. The data which define these characteristics were collected from asexual reproductions carried out by Oglevee Ltd. in Connellsville, Pennsylvania. The plant histories were taken on rooted cuttings potted on Aug. 1, 1988 and flowered Sept. 15, 1988. The plants were blossomed under full light in a greenhouse and color readings were taken indoors under 200–220 foot candles of cool white fluorescent light. Color references are primarily to the R.H.S. Colour Chart of The Royal Horticultural Society of London.

THE PLANT

Classification:

*Botanical.*—Hybrid species.

Form: Semi-dwarf; compact, free basal branching, lateraland cascading growth habit.

Height: 16–17 cm from the media surface.

Growth: Free basal branching, lateral and procumbent habit.

Foliage: Zoning present, stalked leaf attachment.

Leaves:

*Size.*—4–8 cm across.

*Shape.*—Reniform, cordate base.

*Margin.*—Crenate.

*Texture.*—Pubescent; dull (not reflective).

*Color.*—Top: Outer margin: Green group 137B. Zone: Green groujp 139A. Inner margin: Green group 137C. Bottom: Yellow-green group 147B.

*Ribs and veins.*—Palmate venatioln; Yellow-green group 147C.

Petioles: 5–9 cm in length; Yellow-Green group 146C.

Stem:

*Color.*—Yellow-green group 146C.

*Internodes.*—1–2 cm in length.

THE BUD

Shape: Upright;hemispherical cluster.

Size: 1–1.5 cm across.

INFLORESCENCE

Blooming habit: Continuous; upright; very floriferous.

Size: 7–8 cm across.

Borne: 3–7 cm above foliage; florets on pedicel; pedicel on peduncle.

Florets:

*Form.*—Flat to slightly cupped.

*Color.*—Outer petals shade from White group 155A to Red group 56B; Inner petals Red Purple group 62C.

*Petals.*—10–12 in number; separate not united; margin entire obovate; smooth; flat to slightly cupped.

Floret size.—1–1.5 cm across.

*Texture and appearance.*—Smooth; multishades from white to pink.

Petaloids:

*Quantity.*—3–7.

*Shape.*—Narrow, elongated, twisted.

*Color.*—Red-purple group 62D.

Pedicel: 2–3 cm in length; Red-purple group 60A.

Peduncle: Arises from the node, opposite leaf petiole; 12–16.5 cm in length.

*Color.*—Yellow-green group 146B.

Disease resistance: None known.

REPRODUCTIVE ORGANS

Stamens:

*Anthers.*—2 mm in length.

*Filaments.*—6–8 mm in length; white at bottom to light pink at top.

*Pollen.*—Golden brown.

Pistils:

*Number.*—1 with 6 part stigma.

*Length.*—5 mm.

*Stigma.*—1; 6 parted at maturity; Red-purple group.

*Style.*—4–5 mm; white to pale pink.

Ovaries: 3–4 mm in length; 1–2 mm across; very pubescent, pale green; superior.

Fruit: Occasional fruit noted; pale green in color.

This unique variety adds a new dimension to the geranium family. The plant exhibits a neat mound habit that may be used in either hanging baskets or the traditional ground bed. The dark zone compliments the medium green foliage creating an eye catching novelty in the garden. Many small flower clusters create a large continuous bouquet of very pale pink color. In comparing this new variety with the current IVY varieties now on the market, it is more floriferous; a much fuller growth habit; better heat tolerance; and a much better cutting producer.

I claim:

1. A new and distinct variety of Geranium plant substantially as herein shown and described and characterized by lateral and procumbent mound and cascading growth habit, compactness, the presence of zoning, the pale pink inflorescence, the use of either hanging basket or ground bed, its heat tolerance, and a much better cutting producer when compared with available ivy geranium varieties.

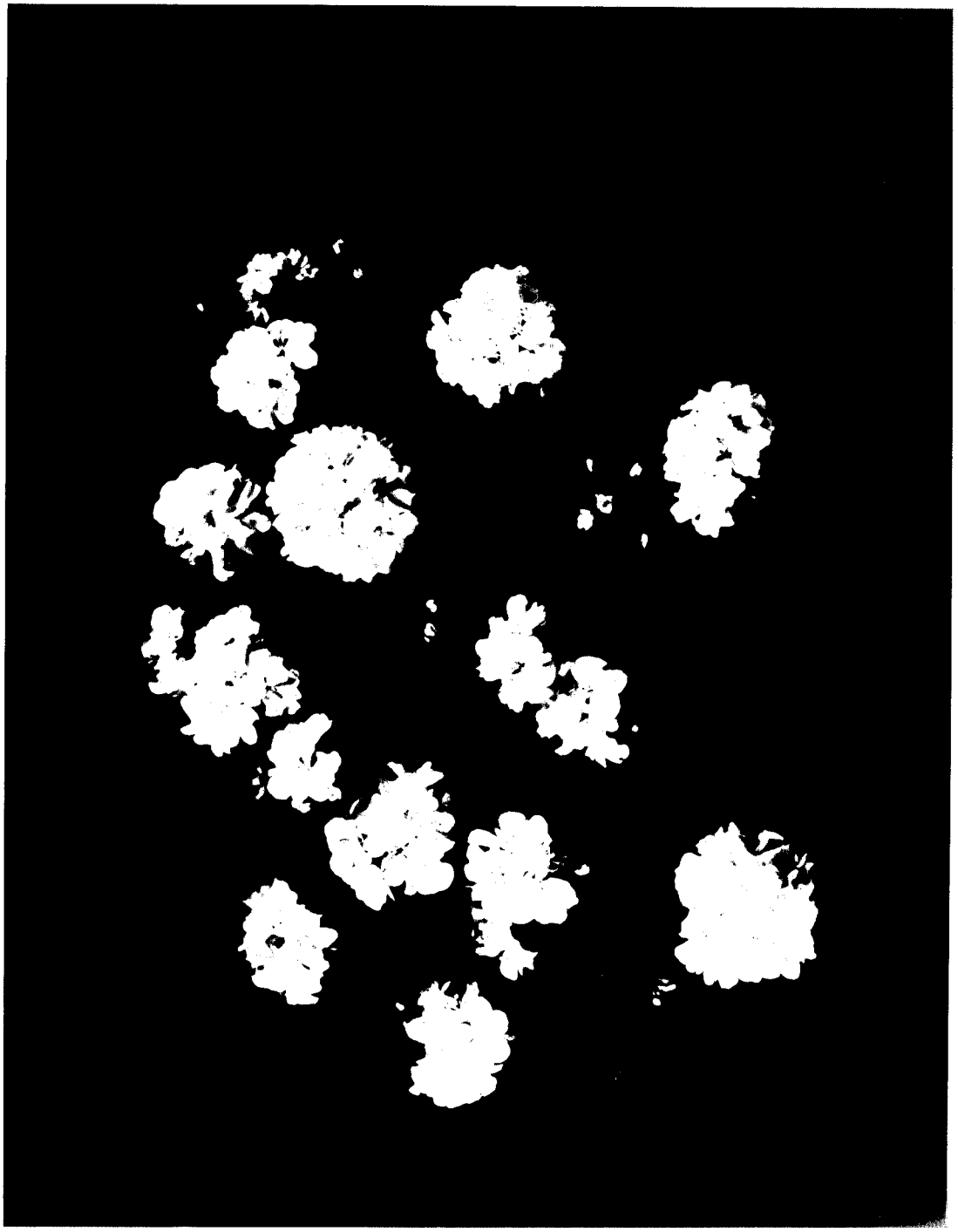

* * * * *